United States Patent

Wu et al.

[11] Patent Number: 5,612,274
[45] Date of Patent: Mar. 18, 1997

[54] METHOD OF PREPARING TRANSALKYLATION CATALYST

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 416,261

[22] Filed: Apr. 4, 1995

[51] Int. Cl.⁶ .................. B01J 23/40; B01J 23/42
[52] U.S. Cl. .................. 502/325; 502/326; 502/339
[58] Field of Search ...................... 502/325, 326, 502/339

[56] References Cited

U.S. PATENT DOCUMENTS

| | | |
|---|---|---|
| 3,594,331 | 7/1971 | Elliott ............................ 252/442 |
| 3,780,122 | 12/1973 | Pollitzer ......................... 260/672 T |
| 3,986,982 | 10/1976 | Crowson et al. ................ 252/415 |
| 4,237,329 | 12/1980 | Kamiyama et al. .............. 585/474 |
| 4,503,023 | 3/1985 | Breck et al. .................... 423/328 |
| 4,923,836 | 5/1990 | Kokayeff et al. ............... 502/79 |
| 5,139,648 | 8/1992 | Lambert ......................... 208/111 |
| 5,364,981 | 11/1994 | Knifton et al. ................ 568/698 |

Primary Examiner—Thurman K. Page
Assistant Examiner—Kathryne E. Shelborne
Attorney, Agent, or Firm—Karl K. Brandes

[57] ABSTRACT

A Group VIII metal-promoted zeolite (preferably Pt-promoted H-mordenite) is contacted with ammonium hexafluorosilicate and hydrogen gas at a temperature of about 100°–450° C. The obtained material is an effective catalyst for the transalkylation of aromatic hydrocarbons.

26 Claims, No Drawings

METHOD OF PREPARING TRANSALKYLATION CATALYST

BACKGROUND OF THE INVENTION

Group VIII noble metal-promoted zeolites, such as platinum-promoted mordenite, are known. They can be used as catalysts in the transalkylation and disproportionation of alkylaromatic hydrocarbons.

It is also known to modify the alumina to silica mole ratio of these zeolites, in particular the hydrogen form of mordenite (referred to as H-mordenite), by treatment with aqueous solutions of fluorine compounds, such as ammonium hexafluorosilicate. The present invention is directed to an improved method of modifying Group VIII noble metal-promoted zeolites.

SUMMARY OF THE INVENTION

It is an object of this invention to provide an improved method of modifying a Group VIII noble metal-promoted zeolite material with ammonium hexafluorosilicate (so as to enhance the catalytic activity of this material, in particular when employed in aromatic transalkylation reactions). It is another object of this invention to treat a platinum-impregnated H-mordenite material with ammonium hexafluorosilicate. Other objects and advantages are apparent from the detailed description of the invention and the appended claims.

In a process for treating a Group VIII noble metal-promoted zeolite material with ammonium hexafluorosilicate, the improvement comprises contacting said material with ammonium hexafluorosilicate and hydrogen gas at a temperature of about 100°–450° C. for a period of time of at least about 5 minutes. In a preferred embodiment, the Group VIII noble metal is platinum and the zeolite is H-mordenite. Preferably, the thus-produced material contains about 1–15 weight-% fluorine (which has been incorporated by the above-described treatment).

DETAILED DESCRIPTION OF THE INVENTION

Any naturally-occurring or synthetic zeolite can be used as the support for a Group VIII noble metal (i.e., Ru, Rh, Pd, Os, Ir, Pt or mixtures thereof, preferably Pt) in the starting material which is employed in the treatment method of this invention. Examples of suitable zeolite species include (but are not limited to) zeolite A, zeolite L, zeolite X, zeolite Y, zeolite rho, zeolite omega, zeolite ZSM-5, zeolite ZSM-11, Zeolon H, mordenite, faujasite, chabazite, offretite, erionite and clinoptilolite. The preferred zeolite support material is H-mordenite (i.e., mordenite in the hydrogen form) which is prepared by ion-exchanging the alkali metal ions contained in mordenite with ammonium ions and subsequent thermal treatment to convert the ammonium-exchanged mordenite to the hydrogen form.

The Group VIII noble metal, in particular platinum, can be incorporated into the zeolite by any suitable, effective means such as by incipient-wetness impregnation or spraying of the zeolite material with a least one dissolved compound of the noble metal (preferably Pt), in particular with an aqueous solution containing hexachloroplatinic acid ($H_2PtCl_6$) and hydrochloric acid, followed by drying (preferably at a temperature of about 20°–150° C. at ambient atmospheric pressure or vacuum conditions, for a time period of about 0.5–100 hours, generally in air), calcining (preferably at a temperature of about 300°–600° C., generally at atmospheric conditions, i.e., about 14–15 psia, for a time period of about 0.5–20 hours), and optionally treating with a gaseous reducing agent (preferably hydrogen gas, at a temperature of about 200°–500° C., for a time period of about 0.5–20 hours). Generally, the Group VIII noble metal content (on an elemental basis) in the starting material is about 0.1–5 weight-% Pt. The starting material can have any suitable shape (preferably cylindrical) and any suitable particle size (preferably about 1–5 mm).

The Group VIII noble metal-promoted zeolite starting material, in particular Pt-promoted H-mordenite, is mixed with solid $(NH_4)_2SiF_6$, generally at a weight ratio of $(NH_4)_2SiF_6$ to the Group VIII noble metal-promoted zeolite in the range of about 0.1:1 to about 1:1, preferably about 0.2:1 to about 0.5:1. The mixture is then heated in the presence of a gas comprising molecular hydrogen, preferably a gas stream containing about 5–100 mole-% of $H_2$. Preferably, the remainder of this gas stream (about 0–95 mole-%) is an inert gas (such as $N_2$, He, Ar and the like, and mixtures thereof). This heating with the $H_2$-containing gas is carried out at a temperature in the range of about 100° C. to about 450° C. (preferably about 200°–400° C., more preferably about 250°–350° C.) for a period of time of at least about 5 minutes, preferably for a time period in the range of about 0.1 hour to about 5 hours (more preferably about 0.5–2 hours). Generally, the hydrogen pressure is about 10–30 psig, preferably about 14–20 psig. Thereafter, the treated material is cooled (generally to room temperature) and stored under an inert gas atmosphere. This treatment results in an increase of the Si:Al atomic ratio of the zeolite support and in the incorporation of fluorine (as chemically bound fluoride) into starting material. The finished product generally contains about 0.5–15 weight-% fluorine (on an elemental basis), preferably about 1–5 weight-% F, and generally has a Si:Al atomic ratio of about 10:1 to about 20:1.

The thus obtained material, in particular Pt/H-mordenite which has been treated with solid $(NH_4)_2SiF_6$ and $H_2$, as described above, can be employed in the transalkylation of aromatic hydrocarbons, such as the disproportionation of toluene to benzene and xylenes, the transalkylation of tri- and tetramethylbenzenes with benzene or toluene so as to form xylenes, generally in the presence of hydrogen gas. Typical operating conditions include a hydrogen pressure of about 0–750 psig, a reaction temperature of about 400°–550° C. (preferably about 450°–500° C.), and a liquid hourly space velocity (LHSV) of the aromatic reagents (preferably a mixture of $C_9+$ aromatic hydrocarbons such as trimethyl- and tetramethylbenzenes as the first reagent, and benzene as the second reagent) of about 0.5 to about 10 (preferably about 1–5) volume aromatic feed per volume catalyst per hour. The reaction product generally comprises unreacted benzene and $C_9^+$ aromatic hydrocarbons, formed toluene, formed ethylbenzene and formed xylene isomers (o-, m- and p-xylene), as will be demonstrated in the examples. The various reaction products can be separated from each other and unconverted feed hydrocarbons by any suitable means, such as fractional distillation.

Reasonable variations and modifications, which would be apparent to those skilled in the art, can be made within the scope of the disclosure and appended claims without departing from the scope of this invention.

The following examples are presented to further illustrate this invention and are not to be construed as unduly limiting the scope of this invention.

EXAMPLE I

This example illustrates the preparation of several platinum-containing H-mordenite transalkylation catalysts.

Catalyst A (Control) was prepared by impregnating (by incipient wetness) 26.54 grams of 1/16" extrudates of H-mordenite (commercially available from PQ Corporation, Valley Forge, Pa.), which had been dried for 16 hours at 125° C. under vacuum conditions (0.1 torr), with a solution of 0.21 gram of hexachloroplatinic acid, 0.21 gram of 38% hydrochloric acid and 15.62 grams of distilled water. The obtained mixture was dried for 1 hour at room temperature in a vacuum oven and then for 1 hour at 125° C. in air, and calcined for 2 hours at 525° C. in air. Thereafter, the catalyst material was heated in a stream of hydrogen gas for 2 hours at 425° C. Catalyst A contained 0.31 weight-% Pt.

Catalyst B (Control) was prepared by treating 10.0 grams of Catalyst A with a solution of 2.66 grams of $(NH_4)_2SiF_6$ in 300 grams of water for 1 hour at 80° C., followed by drying, calcining for 2 hours at 400° C. in air, and heat treatment with flowing hydrogen gas for 1 hour at 300° C. Catalyst B contained about 0.3 weight-% Pt and about 7.2 weight-% F.

Catalyst C (Invention) was prepared by mixing 8.0 grams of Catalyst A with 2.0 grams of solid $(NH_4)_2SiF_6$, heating the mixture in a $He/H_2$ gas stream at a temperature of about 300° C. for 1 hour, and then cooling the material in a pure hydrogen stream from about 300° C. to about 150° C. Catalyst C contained about 0.3 weight-% Pt and about 2.3 weight-% F. A white deposit (probably an aluminum-fluorine compound) was observed at the end of the tubular reactor in which the above-described heat treatment had been carried out.

EXAMPLE II

This example illustrates the use of the catalyst materials described in Example I in the transalkylation of benzene with alkyl-substituted benzenes containing 9+ carbon atoms per molecule.

A stainless steel reactor having an inner diameter of 1 inch and a length of 28 inches was filled with a mixture of 15 cc (about 30.0 g) of Alundum® (inert alumina particles having a surface area of less than 1 m²/g) and 15 cc (about 9–10 g) of each catalyst described in Example I. A hydrocarbon feed prepared by mixing benzene (about 50–59 parts by weight) with a refinery process stream containing $C_9+$ aromatic hydrocarbons (about 41–43 parts by weight). This feed was passed through the solid catalyst bed at a liquid hourly space velocity (LHSV) of about 1.7–2.3 cc feed per cc catalyst per hour. Hydrogen gas was introduced at a rate of about 30 cc/hour so as to provide a heat hydrogen pressure of 500 psig. Pertinent test conditions and results are summarized in Table I.

TABLE I

| Catalyst | Reaction Time (Hrs) | Reaction Temperature (°C.) | Composition of Product (Wt-%)[4] | | | | | % $C_9+$ Conversion |
|---|---|---|---|---|---|---|---|---|
| | | | Benzene | Toluene | Ethylbenzene | Xylenes | $C_9+$ Aromatics | |
| A (Control) | 3.5 | 473 | 40.8 | 16.5 | 4.5 | 7.3 | 27.9 | 35.3[1] |
| | 4.5 | 473 | 40.3 | 17.0 | 4.5 | 7.5 | 27.7 | 35.7[1] |
| | 5.5 | 472 | 40.4 | 14.0 | 4.1 | 6.4 | 32.6 | 24.3[1] |
| | 6.5 | 472 | 37.8 | 16.2 | 4.5 | 7.5 | 31.5 | 27.0[1] |
| B (Control) | 3.5 | 471 | 40.1 | 16.3 | 4.3 | 7.4 | 29.1 | 33.1[2] |
| | 4.6 | 472 | 40.2 | 16.0 | 4.3 | 7.3 | 29.5 | 32.8[2] |
| | 5.5 | 474 | 40.6 | 15.9 | 4.1 | 7.2 | 29.6 | 32.0[2] |
| | 6.6 | 475 | 41.0 | 15.7 | 4.2 | 7.4 | 28.9 | 33.6[2] |
| | 24.2 | 471 | 40.7 | 16.0 | 4.2 | 7.5 | 28.8 | 33.8[2] |
| | 25.2 | 474 | 40.4 | 16.2 | 4.1 | 7.4 | 29.3 | 32.6[2] |
| C (Invention) | 3.6 | 471 | 44.1 | 17.8 | 5.0 | 8.0 | 21.3 | 47.93[3] |
| | 4.6 | 474 | 40.7 | 22.0 | 5.2 | 9.7 | 18.7 | 54.3[3] |
| | 5.8 | 473 | 31.1 | 32.3 | 4.7 | 14.5 | 14.2 | 64.3[3] |
| | 24.1 | 478 | 44.5 | 27.1 | 3.5 | 9.0 | 12.9 | 68.5[3] |

[1]calculation of conversion based on $C_9+$ feed content of 43.1 weight-%.
[2]calculation of conversion based on $C_9+$ feed content of 43.5 weight-%.
[3]calculation of conversion based on $C_9+$ feed content of 40.9 weight-%.
[4]product also contained about 2–3 weight-% cracked products ($C_5-$) and about 0.2–0.5 non-aromatic $C_6-C_7$ cyclics.

Test data clearly show that the invention Catalyst C was considerably more effective in converting $C_9+$ aromatic hydrocarbons, by reaction with benzene, to lower aromatics (in particular xylenes and toluene). As described in Example I, Catalyst C (invention) and Catalyst B (control) had been prepared (by different methods) employing $(NH_4)_2SiF_6$ at approximately the same weight ratio of $(NH_4)_2SiF_6$ to Pt-impregnated alumina (0.25:1 for Catalyst C; 0.27:1 for Catalyst B).

Reasonable variations and modifications which will be apparent to those skilled in the art, can be made within the scope of the disclosure and appended claims without departing from the scope of this invention.

That which is claimed is:

1. A process for treating a Group VIII noble metal-promoted zeolite material with ammonium hexafluorosilicate consisting essentially of the steps of:
    mixing a solid Group VIII noble metal-promoted zeolite material with solid ammonium hexafluorosilicate to obtain a mixture wherein the weight ratio of said solid ammonium hexafluorosilicate to said solid Group VIII noble metal-promoted zeolite material is in the range of about 0.1:1 to about 1:1; and
    heating said mixture in a gas stream containing about 5–100 mole-% of molecular hydrogen at a temperature of about 100° C. to about 450° C. for a period of time of at least about 5 minutes.

2. A process in accordance with claim 1, wherein said Group VIII noble metal-promoted zeolite material is platinum-promoted mordenite.

3. A process in accordance with claim 1, wherein said time period is about 0.1–5 hours, and said Group VIII noble metal-promoted zeolite material is platinum-promoted H-mordenite.

4. A process in accordance with claim 3, wherein the platinum content in said platinum-promoted H-mordenite is about 0.1–5 weight-% Pt.

5. A process in accordance with claim 3, wherein said weight ratio of said solid ammonium hexafluorosilicate to said Group VIII noble-metal promoted zeolite material is in the range of about 0.2:1 to about 0.5:1.

6. A process in accordance with claim 3, wherein said heating of said mixture of said solid platinum-promoted H-mordenite and said solid ammonium hexafluorosilicate with said gas stream is carried out at a temperature of about 200°–400° C. for a time period of about 0.1–5 hours.

7. A process in accordance with claim 6, wherein said heating is carried out at a temperature of about 250°–350° C. for a time period of about 0.5–2 hours.

8. A process in accordance with claim 6, wherein the hydrogen pressure during said heating is about 10–30 psig.

9. A process in accordance with claim 1, wherein said gas stream comprises about 0–95 mole-% of an inert gas.

10. A process in accordance with claim 1, wherein the material produced by said process contains about 0.5–15 weight-% fluorine.

11. A process in accordance with claim 10, wherein said material produced by said process contains about 1–5 weight-% fluorine.

12. A process in accordance with claim 11, wherein said material produced by said process has a silicon to aluminum atomic ratio of about 10:1 to about 20:1.

13. A process for treating a Group VIII noble metal-promoted zeolite with ammonium hexafluorosilicate consisting essentially of the steps of:

(A) treating a solid Group VIII noble metal-promoted zeolite material with a gaseous reducing agent at a temperature of about 200°–500° C.;

(B) mixing the reduced, solid Group VIII noble metal-promoted zeolite material obtained in step (A) with solid ammonium hexafluorosilicate to obtain a mixture wherein the weight ratio of said solid ammonium hexafluorosilicate to said reduced, solid Group VIII noble metal-promoted zeolite material is in the range of about 0.1:1 to about 1:1; and (C) heating the mixture obtained in step (B) in a gas stream containing about 5–100 mole-% of molecular hydrogen at a temperature of about 100° C. to about 450° C. for a time period of at least about 5 minutes.

14. A process in accordance with claim 13 wherein said gaseous reducing agent used in step (A) is hydrogen gas.

15. A process in accordance with claim 14, wherein said solid Group VIII noble metal-promoted zeolite material which is used as the starting material in step (A) has been calcined at a temperature of about 300°–600° C. for a time period of about 0.5–20 hours, and said treating with said gaseous reducing agent in step (A) is carried out for a time period of about 0.5–20 hours.

16. A process in accordance with claim 14, wherein said solid Group VIII noble metal-promoted zeolite material which is used as the starting material in step (A) is platinum-promoted mordenite.

17. A process in accordance with claim 16, wherein said Group VIII noble metal-promoted zeolite material which is used as the starting material in step (A) is platinum-promoted H-mordenite, and the time period of step (C) is about 0.1–5 hours.

18. A process in accordance with claim 17, wherein the platinum content in said platinum-promoted H-mordenite which is used as the starting material in step (A) is about 0.1–5 weight-% Pt.

19. A process in accordance with claim 17, wherein said weight ratio of said solid ammonium hexafluorosilicate to said reduced, solid Group VIII noble metal-promoted zeolite material in said mixture obtained in step (B) is in the range of about 0.2:1 to about 0.5:1.

20. A process in accordance with claim 17, wherein step (C) is carried out at a temperature of about 200°–400° C. for a time period of about 0.1–5 hours.

21. A process in accordance with claim 20, wherein step (C) is carried out at a temperature of about 250°–350° C. for a time period of about 0.5–2 hours.

22. A process in accordance with claim 20, wherein the hydrogen pressure in step (C) is about 10–30 psig.

23. A process in accordance with claim 20, wherein said gas stream comprises about 0–95 mole-% of an inert gas.

24. A process in accordance with claim 14, wherein the material produced by said process contains about 0.5–15 weight-% fluorine.

25. A process in accordance with claim 14, wherein said material produced by said process contains about 1–5 weight-% fluorine.

26. A process in accordance with claim 25, wherein said material produced by said process has a silicon to aluminum atomic ratio of about 10:1 to about 20:1.

\* \* \* \* \*